United States Patent
Hagenow et al.

(10) Patent No.: US 8,226,733 B2
(45) Date of Patent: Jul. 24, 2012

(54) TWO-PHASE DEVELOPER

(75) Inventors: Susanne Hagenow, Hamburg (DE); Astrid Kleen, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/245,000

(22) Filed: Sep. 26, 2011

(65) Prior Publication Data

US 2012/0012129 A1 Jan. 19, 2012

Related U.S. Application Data

(63) Continuation of application No. PCT/EP2010/052602, filed on Mar. 2, 2010.

(30) Foreign Application Priority Data

Mar. 27, 2009 (DE) .......... 10 2009 001 937

(51) Int. Cl.
*A61Q 5/10* (2006.01)
(52) U.S. Cl. ............. 8/405; 8/111; 8/431; 8/501; 8/581; 8/632
(58) Field of Classification Search ............... 8/405, 111, 8/431, 501, 581, 632
See application file for complete search history.

(56) References Cited

U.S. PATENT DOCUMENTS

| 5,817,155 | A * | 10/1998 | Yasuda et al. ............... 8/406 |
| 6,238,653 | B1 | 5/2001 | Narasimhan et al. |
| 2003/0211953 | A1 | 11/2003 | Glenn et al. |
| 2008/0172807 | A1 | 7/2008 | Brun |

FOREIGN PATENT DOCUMENTS

FR 2910309 A1 6/2008

OTHER PUBLICATIONS

Schrader, Karlheinz. Grundlagen und Rezepturen der Kosmetika (Fundamentals and Formulations of Cosmetics), 2, Hüthig Buch Verlag GmbH, Heidelberg 1989.

* cited by examiner

*Primary Examiner* — Eisa Elhilo
(74) *Attorney, Agent, or Firm* — David P. LeCroy

(57) ABSTRACT

Cosmetic preparation for keratinic fibers, particularly human hair, having two phases separated from each other, wherein one of the phases is an aqueous phase and the other phase a hydrophobic phase. These preparations contain at least one chemical oxidizing agent and at least one silicone oil. The agents, in their function as oxidizing preparations, are used as a developer preparation for oxidation dyes or brightening agents.

11 Claims, No Drawings

TWO-PHASE DEVELOPER

CROSS REFERENCE TO RELATED APPLICATIONS

This is a continuation of International Patent Application No. PCT/EP2010/052602 filed 2 Mar. 2010, which claims priority to German Patent Application No. 10 2009 001 937.5 filed 27 Mar. 2009, both of which are incorporated herein by reference.

The present application provides a cosmetic preparation for keratinic fibers, particularly human hair, having two phases separated from each other. One of the phases is an aqueous phase and the other phase is a hydrophobic phase. These preparations contain at least one chemical oxidizing agent and at least one silicone oil. As oxidizing preparations, these agents are used as a developer preparation for oxidation dyes or lightening agents. The present invention therefore also provides a method for changing the color of keratinic fibers, wherein the color-changing agent according to the invention is applied to keratinic fibers.

Changing the shape and color of hair is an important area of modern cosmetics. It allows the appearance of the hair to be adapted both to the latest fashion trends and to the personal preferences of the individual. In addition to providing the desired coloring and shaping capacity, these agents should give rise to the minimum possible damage to the hair and should preferably even have additional care properties.

One skilled in the art is familiar with various coloring systems for providing color-changing cosmetic agents, particularly for the skin or keratin-containing fibers such as human hair, depending on the requirements of the coloring process. For permanent, intense colors with corresponding fastness properties, oxidation coloring agents are used. Such coloring agents typically contain oxidation dye precursors known as developer components and coupler components which, under the influence of oxidizing agents or atmospheric oxygen, form the actual dyes with one another. Oxidation coloring agents produce outstanding, long-lasting coloring results. For temporary colors, coloring or tinting agents containing substantive dyes as the coloring component are commonly used.

In addition to coloring their hair, many consumers specifically wish to lighten or bleach their natural hair color because blonde hair is considered to be attractive and desirable from a fashion perspective. If substrates are to be lightened or bleached, dyes coloring the substrate are mostly decolorized by oxidation using corresponding oxidizing agents such as hydrogen peroxide.

Oxidative hair treatment agents in particular, despite their advantageous coloring and/or lightening properties, can be disadvantageous for the user. Firstly, use of oxidizing agents can damage the hair structure and surface of the hair. For example, the hair becomes brittle, its elasticity decreases and it becomes less easy to comb. This damage increases with the length of application. Secondly, oxidative coloring agents generally require an alkaline pH range for pigment removal, particularly from pH 9.0 to pH 10.5. Splaying of the external cuticle of the hair associated with the basic pH can result in an unpleasant surface sensitivity of the hair, making it more difficult to comb when wet and dry. For the consumer, this results in an increased necessity to use additional post-treatment agents such as conditioning agents. In addition, hair structure can be also affected by external environmental influences. These include mechanical and thermal influences, such as combing and blow-drying. Weather influences such as wind, rain and UV radiation in sunlight, and additional external stresses such as chlorinated swimming pool water or perspiration can likewise contribute to damage to the hair structure and hair surface. To improve the condition of the fibers, it has long been conventional practice to subject the fibers to a special post-treatment following the color-changing treatment. Here the hair is treated with special active ingredients such as quaternary ammonium salts or special polymers, typically in the form of a rinse. Depending on the formulation, combability, hold and fullness of the hair are improved and the number of split ends is reduced by this treatment. One difficulty here is that many of the conventional care substances and active agents to reduce hair damage can be inadequately stable under the oxidative conditions of a hair treatment agent.

Therefore, there is still a need for caring preparations for the color-changing treatment of fibers. The present invention therefore provides a color-changing agent for which the aforementioned disadvantages of customary color-changing agents are reduced. In particular, the color-changing agents can provide protection against oxidative damage to the hair structure and hair surface. Caring properties of the agents are particularly desirable, allowing the user to dispense with the use of additional conditioning and post-treatment agents. Accordingly, the agents should also be suitable for stabilizing care substances and active agents that are inadequately stable under oxidative conditions, enabling them to be used in the oxidative hair treatment. It is moreover desirable for the user if, in addition to the objective care performance, the agents reveal visual evidence of the care treatment.

It has now been found that hair damage can be minimized or even a hair care effect achieved by means of special two-phase cosmetic, oxidative preparations for use in color-changing agents for keratinic fibers, particularly human hair.

The present invention firstly provides a cosmetic agent for treating keratinic fibers and having at least two phases separated from each other. The first phase (I) is an aqueous phase containing at least one chemical oxidizing agent, and the second phase (II) is a hydrophobic phase containing at least one silicone oil.

Keratin-containing or keratinic fibers according to the invention refer to fur, wool, feathers and particularly human hair. Although use of the agent according to the invention is primarily suitable for coloring and/or lightening keratin-containing fibers, there is nothing in principle to preclude a use in other fields.

A critical feature of the preparation according to the invention is its two-phase character, the two phases being immiscible with each other. The two phases are preferably present in two layers, one above the other.

In the preparation, phase (I) is preferably present in at least the same percentage by weight as phase (II). Phase (I) is more preferably present in excess. The weight ratio of phase (I) to phase (II) is preferably from 99 to 1 to 50 to 50, more preferably from 98 to 2 to 80 to 20, and even more preferably from 95 to 5 to 90 to 10.

According to the present invention, phase (I) has an aqueous or aqueous-alcoholic carrier. Within the context of the present invention, aqueous-alcoholic carriers refer to water-containing compositions containing 3 to 70 wt. %, based on total weight of the application mixture, of a $C_1$ to $C_4$ alcohol, particularly ethanol or isopropanol. An aqueous carrier within the meaning of the invention contains at least 30 wt. %, particularly at least 50 wt. %, of water, based on total weight of the application mixture.

Phase (I) also contains at least one chemical oxidizing agent. The term "chemical oxidizing agent" is intended to show that it is a deliberately added oxidizing agent and not an oxidizing agent present in the atmosphere such as atmospheric oxygen. Hydrogen peroxide is preferably used as the oxidizing agent according to the invention. Hydrogen peroxide is preferably used as an aqueous solution or in the form of a solid addition compound of hydrogen peroxide with inorganic or organic compounds such as sodium perborate, sodium percarbonate, magnesium percarbonate, sodium percarbamide, polyvinyl pyrrolidinone.n $H_2O_2$ (n is a positive whole number greater than 0), urea peroxide and melamine peroxide. Particularly preferred aqueous phases (I) according to the invention contain aqueous hydrogen peroxide solutions. The concentration of a hydrogen peroxide solution is determined by legal requirements and by the desired effect. 3 wt. % to 12 wt. % solutions in water are preferably used as the aqueous phase.

Preparations according to the invention advantageously contain hydrogen peroxide. Preferred agents for changing the color of keratinic fibers contain 0.5 to 18 wt. %, preferably 1 to 15 wt. %, more preferably 2.5 to 12 wt. %, and in particular 3 to 9 wt. % of hydrogen peroxide (calculated as 100% $H_2O_2$).

According to the present invention, phase (II) is hydrophobic in nature. Hydrophobic phase (II) according to the invention is immiscible with the aqueous phase (I) containing the oxidizing agent. Hydrophobic phases, also known as lipophilic phases, contain adipoids, which are usually non-polar, organic compounds such as hydrocarbon compounds, long-chain triglycerides, esters or ethers and perhalogenated compounds. A further class of substance suitable for forming hydrophobic phases is silicones, particularly silicone oils. The hydrophobic phase (II) of the present invention contains at least one silicone oil. "Silicone oil" refers to silicones that are liquid at room temperature and under normal pressure. Silicones have siloxane bonds (which is why they are also known as siloxane). Suitable silicone oils are those having no or only very slight water solubility.

Silicone oils are preferably chosen from at least one representative of
(i) polyalkylsiloxanes, polyarylsiloxanes and polyalkylarylsiloxanes, which are volatile or non-volatile, straight-chain, branched or cyclic, crosslinked or non-crosslinked;
(ii) polysiloxanes, which in their general structure contain one or more lipophilic, organofunctional groups chosen from:
  a) (per)fluorinated groups;
  b) alkoxylated groups;
  c) carboxylic acid esters;
  d) aryl ethers;
  e) acyloxyalkyl groups;
(iii) linear polysiloxane(A)-polyoxyalkylene(B) block copolymers of the type $(A-B)_n$, where n>3;
(iv) grafted silicone polymers having a non-silicone-containing, organic framework consisting of an organic main chain formed from organic monomers containing no silicone, onto which at least one polysiloxane macromer has been grafted in the chain and optionally on at least one chain end;
(v) grafted silicone polymers having a polysiloxane framework, onto which non-silicone-containing, organic monomers have been grafted, which have a polysiloxane main chain onto which at least one organic macromer containing no silicone has been grafted in the chain and optionally on at least one of its ends;
(vi) or mixtures thereof.

Particularly preferred cosmetic preparations according to the invention contain at least one silicone of formula (Si-1)

$(CH_3)_3Si—[OSi(CH_3)_2]_x—OSi(CH_3)_3$ (Si-1), wherein x is a number from 0 to 100, preferably from 0 to 50, more preferably from 0 to 20 and in particular 0 to 10.

Preferred cosmetic preparations used according to the invention contain a silicone of the above formula (Si-1). According to INCI nomenclature, these silicones are known as dimethicones. The following compounds are preferably used as the silicone of formula (Si-1): $(CH_3)_3Si—OSi(CH_3)_3$; $(CH_3)_3Si—OSi(CH_3)_2—OSi(CH_3)_3$; $(CH_3)_3Si—[OSi(CH_3)_2]_2—OSi(CH_3)_3$; $(CH_3)_3Si—[OSi(CH_3)_2]_3—OSi(CH_3)_3$; $(CH_3)_3Si—[OSi(CH_3)_2]_4—OSi(CH_3)_3$; $(CH_3)_3Si—[OSi(CH_3)_2]_5—OSi(CH_3)_3$; $(CH_3)_3Si—[OSi(CH_3)_2]_6—OSi(CH_3)_3$; $(CH_3)_3Si—[OSi(CH_3)_2]_7—OSi(CH_3)_3$; $(CH_3)_3Si—[OSi(CH_3)_2]_8—OSi(CH_3)_3$; $(CH_3)_3Si—[OSi(CH_3)_2]_9—OSi(CH_3)_3$; $(CH_3)_3Si—[OSi(CH_3)_2]_{10}—OSi(CH_3)_3$; $(CH_3)_3Si—[OSi(CH_3)_2]_{11}—OSi(CH_3)_3$; $(CH_3)_3Si—[OSi(CH_3)_2]_{12}—OSi(CH_3)_3$; $(CH_3)_3Si—[OSi(CH_3)_2]_{13}—OSi(CH_3)_3$; $(CH_3)_3Si—[OSi(CH_3)_2]_{14}—OSi(CH_3)_3$; $(CH_3)_3Si—[OSi(CH_3)_2]_{15}—OSi(CH_3)_3$; $(CH_3)_3Si—[OSi(CH_3)_2]_{16}—OSi(CH_3)_3$; $(CH_3)_3Si—[OSi(CH_3)_2]_{17}—OSi(CH_3)_3$; $(CH_3)_3Si—[OSi(CH_3)_2]_{18}—OSi(CH_3)_3$; $(CH_3)_3Si—[OSi(CH_3)_2]_{19}—OSi(CH_3)_3$; $(CH_3)_3Si—[OSi(CH_3)_2]_{20}—OSi(CH_3)_3$, with $(CH_3)_3Si—OSi(CH_3)_3$, $(CH_3)_3Si—OSi(CH_3)_2—OSi(CH_3)_3$ and/or $(CH_3)_3Si—[OSi(CH_3)_2]_2—OSi(CH_3)_3$ being particularly preferred.

Preferred agents according to the invention can also contain mixtures of the aforementioned silicones.

Preferred silicones can have viscosities at 20° C. of 0.2 to 2 $mm^2s^{-1}$, with silicones having viscosities of 0.5 to 1 $mm^2s^{-1}$ being particularly preferred.

Cyclic dimethicones referred to under INCI as cyclomethicones can also be used. Cosmetic or dermatological preparations according to the invention are preferred here which contain at least one silicone of formula (Si-2),

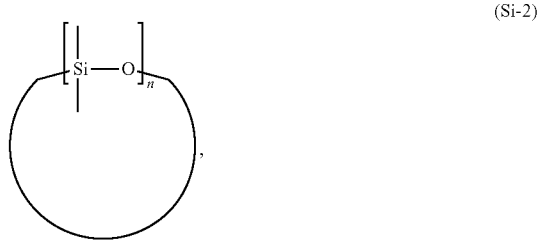

wherein x is a number from 0 to 200, preferably from 0 to 10, more preferably from 0 to 7 and in particular 0, 1, 2, 3, 4, 5 or 6.

Branched silicones can also be used according to the invention. A preferred branched silicone according to the invention is the silicone of formula $[(H_3C)_3SiO]_3Si-Ph$ known by the INCI name Phenyl Trimethicone, sold, for example, under the trade name DC 556.

Agents that are likewise preferably used according to the invention contain at least one silicone of formula (Si-3), $R_3Si—[O—SiR_2]_x—(CH_2)_n—[O—SiR_2]_y—O—SiR_3$ (Si-3), wherein $R_3$ is identical or different residues from the group —H, -phenyl, -benzyl, —$CH_2$—$CH(CH_3)Ph$, $C_1$-$C_{20}$ alkyl residues, preferably —$CH_3$, —$CH_2CH_3$, —$CH_2CH_2CH_3$, —$CH(CH_3)_2$, —$CH_2CH_2CH_2H_3$, —$CH_2CH(CH_3)_2$, —$CH(CH_3)CH_2CH_3$, —$C(CH_3)_3$; x and y are each a number from 0 to 200, preferably from 0 to 10, more preferably from 0 to 7 and in particular 0, 1, 2, 3, 4, 5 or 6; and n is a number from 0 to 10, preferably from 1 to 8 and in particular 2, 3, 4, 5, 6.

Preferred agents contain a hydrophobic phase (II) having at least one silicone oil chosen from dimethicones and cyclomethicones.

Agents according to the invention preferably contain silicone oil in an amount from 0.1 to 50 wt. %, preferably 0.5 to 30 wt. % and in particular 1 to 15 wt. %, based on total weight of the ready-to-use agent.

To improve the separation of the hydrophilic phase (I) and the hydrophobic phase (II), the agents preferably contain only a small proportion of interfacially active substances. Emulsifiers and surfactants are classed as interfacially active substances within the meaning of the invention. Interfacially active substances have hydrophobic and hydrophilic structural features and thus allow intermixing of the phases, with formation of micelles and stable emulsions. As the present invention explicitly encompasses no emulsions but rather contains two phases separated from each other, it has proven particularly advantageous for the agent to contain non-ionic, anionic, zwitterionic and/or amphoteric surfactants and/or emulsifiers in a total weight of less than 5 wt. %, preferably less than 1 wt. %, based on total weight of the ready-to-use agent. Agents free of interfacially active substances are particularly advantageous.

All anionic surface-active substances suitable for use on the human body are suitable as anionic surfactants within the meaning of the invention. These have a water-solubilizing anionic group such as a carboxylate, sulfate, sulfonate or phosphate group and a lipophilic alkyl group having approximately 8 to 30 C atoms. The molecule can additionally contain glycol or polyglycol ether groups, ester, ether and amide groups and hydroxyl groups. Examples of such anionic surfactants, in each case in the form of the sodium, potassium and ammonium and also mono-, di- and trialkanolammonium salts having 2 to 4 C atoms in the alkanol group, are linear and branched fatty acids having 8 to 30 C atoms (soaps); ether carboxylic acids, particularly of the formula $RO(CH_2CH_2O)_xCH_2COOH$, wherein R is a linear alkyl group having 8 to 30 C atoms and x=0 or 1 to 16; acyl sarcosides; acyl taurides; acyl isethionates; sulfosuccinic acid mono- and -dialkyl esters and sulfosuccinic acid monoalkyl polyoxyethyl esters; linear alkane sulfonates; linear α-olefin sulfonates; sulfonates of unsaturated fatty acids; α-sulfofatty acid methyl esters of fatty acids; alkyl sulfates and alkyl ether sulfates, particularly of the formula $RO(CH_2CH_2O)_xSO_3H$, wherein R is a linear alkyl group having 8 to 30 C atoms and x is 0 or a number from 1 to 12; mixtures of surface-active hydroxy sulfonates; sulfated hydroxyalkyl polyethylene and/or hydroxyalkylene propylene glycol ethers; esters of tartaric acid and citric acid with alcohols; alkyl and/or alkenyl ether phosphates of the formula $RO(C_2H_4O)_xP(=O)(OH)(OR')$, wherein R is an aliphatic, optionally unsaturated hydrocarbon residue having 8 to 30 carbon atoms, R' is hydrogen, a residue $(CH_2CH_2O)_yR$, and x and y independently of each other are a number from 1 to 10; sulfated fatty acid alkylene glycol esters of the formula $RC(O)O(alkO)_nSO_3H$, wherein R is a linear or branched, aliphatic, saturated and/or unsaturated alkyl residue having 6 to 22 C atoms, alk is $CH_2CH_2$, $CHCH_3CH_2$ and/or $CH_2CHCH_3$ and n is a number from 0.5 to 5; and monoglyceride sulfates and monoglyceride ether sulfates.

Surface-active compounds classified as zwitterionic surfactants are those having at least one quaternary ammonium group and at least one carboxylate, sulfonate or sulfate group in the molecule. Examples of such zwitterionic surfactants are betaines such as N-alkyl-N,N-dimethylammonium glycinates, for example cocoalkyl dimethylammonium glycinate, N-acyl aminopropyl-N,N-dimethylammonium glycinates, for example cocoacylaminopropyl dimethylammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name Cocamidopropyl Betaine.

Amphoteric surfactants are understood to be surface-active compounds which, in addition to a $C_8$-$C_{24}$ alkyl or acyl group, contain at least one free amino group and at least one —COOH or —$SO_3H$ group in the molecule and are capable of forming internal salts. Conventional amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids, each having approximately 8 to 24 C atoms in the alkyl group. Amphoteric surfactants include N-cocoalkyl aminopropionate, cocoacylaminoethyl aminopropionate and $C_{12}$-$C_{18}$ acyl sarcosine.

Non-ionic surfactants and emulsifiers contain as a hydrophilic group a polyol group a polyalkylene glycol ether group or a combination of a polyol and polyglycol ether group, for example. Such compounds include addition products of 1 to 50 mol of ethylene oxide and/or 0 to mol of propylene oxide with linear and branched fatty alcohols having 8 to 30 C atoms, with fatty acids having 8 to 30 C atoms and with alkyl phenols having 8 to 15 C atoms in the alkyl group; addition products of 1 to 50 mol of ethylene oxide and/or 0 to 5 mol of propylene oxide with linear and branched fatty alcohols having 8 to 30 C atoms, with fatty acids having 8 to 30 C atoms and with alkyl phenols having 8 to 15 C atoms in the alkyl group, end-capped with a methyl or C2 to C6 alkyl residue, such as the types available under the commercial names Dehydrol LS, Dehydrol LT (Cognis); polyglycerol esters and alkoxylated polyglycerol esters, such as poly(3)glycerol diisostearate (commercial product: Lameform TGI (Henkel)) and poly(2)glycerol polyhydroxystearate (commercial product: Dehymuls PGPH (Henkel)); polyol fatty acid esters, such as the commercial product Hydagen HSP (Cognis) or Sovermol types (Cognis); more highly alkoxylated, propoxylated and in particular ethoxylated, mono-, di- and triglycerides having a degree of alkoxylation of greater than 5, such as for example glycerol monolaurate+20 ethylene oxide and glycerol monostearate+20 ethylene oxide; amine oxides; hydroxyl mixed ethers; sorbitan fatty acid esters and addition products of ethylene oxide with sorbitan fatty acid esters such as for example polysorbates and sorbitan monolaurate+20 ethylene oxide (EO); sugar fatty acid esters and addition products of ethylene oxide with sugar fatty acid esters; addition products of ethylene oxide with fatty acid alkanol amides and fatty amines; fatty acid-N-alkyl glucamides; alkyl phenols and alkyl phenol alkoxylates having 6 to 21, in particular 6 to 15 carbon atoms in the alkyl chain and 5 to 30 ethylene oxide and/or propylene oxide units; alkyl polyglycosides corresponding to the general formula RO—(Z)x, in which R is alkyl, Z is sugar and x is the number of sugar units.

Non-ionic emulsifiers within the meaning of the invention also include the polymerization products of ethylene oxide and propylene oxide with saturated or unsaturated fatty alcohols; fatty acid esters of polyhydric alcohols with saturated or unsaturated fatty acids; alkyl esters of saturated or unsaturated fatty acids or alkyl phenols and alkoxylates thereof; particularly ethylene glycol ethers of fatty alcohols; mixed ethylene and propylene glycol ethers with fatty alcohols; fatty acid esters with sorbitan and polyethylene glycol; esters of non-hydroxylated $C_6$-$C_{30}$ alkyl monocarboxylic acids with polyethylene glycol; and addition products of alkyl phenols with ethylene oxide and/or propylene oxide.

To separate the hydrophilic and hydrophobic phase in the agent, it can furthermore be advantageous to additionally add electrolytes to the agent. Electrolytes are conventionally understood to be charged, ionic, inorganic and organic compounds having no or only a very slightly pronounced hydrophobic component. Preferred electrolytes are readily water-soluble salts, in particular alkali metal and alkaline-earth metal salts of mineral acids and organic acids. Examples thereof are sodium chloride, sodium sulfate, sodium hydrogen sulfate, sodium carbonate, sodium hydrogen carbonate, sodium citrate, magnesium chloride, magnesium sulfate, magnesium carbonate and magnesium hydrogen carbonate.

In the agent according to the invention, oil-soluble constituents largely accumulate in the silicone oil-containing phase (II) and so do not come into direct contact with the oxidizing agent-containing phase (I). This is particularly advantageous for stabilizing oxidatively unstable care substances in the agent. Such preferred care substances are therefore oil-soluble care substances, oil-soluble vitamins and triglycerides, particularly those containing one or more unsaturated carbon-carbon bonds.

A particular embodiment of the present invention thus has the characterizing feature that the agent additionally contains at least one care component that is largely soluble in the silicone oil and chosen from oil-soluble care substances, oil-soluble vitamins and triglycerides.

Oil-soluble care substances include cosmetically effective terpenes and terpenoids, such as bisabolol, and ubiquinones, such as coenzyme Q-10.

Oil-soluble vitamins are in particular the compounds known under the collective names vitamin A, vitamin D, vitamin E and vitamin K. A preferred agent according to the invention therefore contains at least one oil-soluble vitamin chosen from vitamin A, vitamin D, vitamin E and/or vitamin K as well as vitamin P. Vitamin A includes retinoids, particularly all-trans retinol. Vitamin D, also known as calciferols, includes 7,8-didehydrosterol derivatives, particularly the compounds known as cholecalciferol (vitamin $D_3$, calciol), ergocalciferol (vitamin $D_2$, ercalciol), 7,8-didehydrocholesterol (provitamin $D_3$, procalciol, procholecalciferol) and ergosterol (provitamin $D_2$). Other vitamin D analogs that can be used are calcidiol (25-hydroxycholecalciferol), calcitriol, hydroxycalcidiol and vitamin $D_1$ (ergocalciferol and lumisterol). Vitamin E is the collective name for tocopherols and includes the chemical compounds α-tocopherol, β-tocopherol, γ-tocopherol, δ-tocopherol and α-tocotrienol, β-tocotrienol, γ-tocotrienol and δ-tocotrienol. Vitamin K is the collective name for various compounds with vitamin K activity which derive from 2-methyl-1,4-naphthoquinone (vitamin $K_3$). Preferred representatives are vitamin $K_{1(20)}$ (2-methyl-3-phytyl-1,4-naphthoquinone), phylloquinone (abbreviation: K),], vitamin $K_{2(35)}$ (3-all-trans farnesylgeranylgeranyl-2-methyl-1,4-naphthoquinone), vitamin $K_3$ (2-methyl-1,4-naphthoquinone, menadione, menaphthone) and the derived analogs vitamin $K_4$ (2-methyl-1,4-naphthalenediol), vitamin $K_5$ (4-amino-2-methyl-1-naphthol), vitamin $K_6$ (2-methyl-1,4-naphthalenediamine) and vitamin $K_7$ (4-amino-3-methyl-1-naphthol). Vitamin P is a collective name for rutins, particularly bioflavonoids such as troxerutin (vitamin $P_4$) and hesperidin.

Triglycerides are esters of glycerol, which are the main constituents of natural oils. Preferred triglycerides are those having at least one ester of an unsaturated fatty acid. Preferred unsaturated fatty acids are oleic acid, linoleic acid and linolenic acid.

Agents according to the invention are preferably used to change the color of keratinic fibers. To that end the two-phase agent according to the invention (M1) is mixed with a further agent (M2) having at least one color-changing component, and the resulting ready-to-use preparation is applied to the keratinic fibers.

Additional bleaching strength intensifiers which intensify the effect of the oxidizing agent from phase (I) of the two-phase agent as lightening agents along with coloring components serve as the color-changing component in agent (M2).

In one embodiment, the agent according to the invention (M2) contains an additional bleaching strength intensifier. In the context of this invention peroxo compounds and compounds which under perhydrolysis conditions give rise to aliphatic peroxocarboxylic acids and/or substituted perbenzoic acid, carbonic acid derivatives, alkyl carbonates and carbamates, silyl carbonates and carbamates can be used as additional bleaching strength intensifiers.

The bleaching strength intensifier is preferably chosen from ammonium peroxodisulfate, alkali metal peroxodisulfates, ammonium peroxomonosulfate, alkali metal hydrogen peroxomonosulfates, alkali metal peroxodiphosphates and alkaline-earth metal peroxides. Particularly preferred bleaching strength intensifiers are ammonium peroxodisulfate, potassium peroxodisulfate, sodium peroxodisulfate, potassium hydrogen peroxomonosulfate, potassium peroxodiphosphate, magnesium peroxide and barium peroxide. Particularly preferred agents contain as bleaching strength intensifier at least one inorganic salt chosen from peroxomonosulfates and/or peroxodisulfates. In the work on the present invention it has furthermore proved particularly preferable for the agents to have at least two different peroxodisulfates. Preferred peroxodisulfate salts are combinations of ammonium peroxodisulfate and potassium peroxodisulfate and/or sodium peroxodisulfate. The peroxo compounds are included in an amount of from 0.1 to 25 wt. %, particularly from 0.5 to 15 wt. %, based on total weight of the ready-to-use agent.

Use of persulfate salts or peroxodisulfate salts generally takes place anhydrously and in the form of an optionally dedusted powder, paste or a pressed molding. Anhydrous agents (M2) can contain a further bleaching strength intensifier instead of and/or in addition to the solid peroxo compounds.

Compounds which under perhydrolysis conditions yield aliphatic peroxocarboxylic acids having preferably 1 to 10 C atoms, particularly 2 to 4 C atoms, and/or optionally substituted perbenzoic acid can be used as bleach intensifiers. Substances bearing O and/or N acyl groups of the cited C atomic number and/or optionally substituted benzoyl groups are suitable. Polyacylated alkylene diamines, particularly tetraacetyl ethylene diamine (TAED), acylated triazine derivatives, particularly 1,5-diacetyl-2,4-dioxohexahydro-1,3,5-triazine (DADHT), acylated glycolurils, particularly tetraacetyl glycoluril (TAGU), N-acylimides, particularly N-nonanoyl succinimide (NOSI), acylated phenol sulfonates, particularly n-nonanoyl- or isononanoyloxybenzenesulfonate (n- or i-NOBS), carboxylic anhydrides, particularly phthalic anhydride, acylated polyhydric alcohols, particularly triacetin, ethylene glycol diacetate and 2,5-diacetoxy-2,5-dihydrofuran, are preferred.

Carbonate salts or hydrogen carbonate salts can preferably be used according to the invention as bleach intensifiers of the carbonic acid derivative type. These are preferably chosen from ammonium, alkali metal (particularly sodium and potassium) and alkaline-earth metal (particularly magnesium and calcium) carbonate salts or hydrogen carbonate salts.

Particularly preferred carbonate or hydrogen carbonate salts are ammonium hydrogen carbonate, ammonium carbonate, sodium hydrogen carbonate, sodium carbonate, potassium hydrogen carbonate, potassium carbonate, magnesium carbonate and calcium carbonate. These particularly preferred salts can be used as bleaching strength intensifiers alone or in mixtures of at least two representatives thereof.

Although in general there are no restrictions regarding the formulation of the further agent (M2), it has proved preferable according to the invention if the agent (M2) is anhydrous. Anhydrous refers to a water content relative to the agent (M2) of less than 5 wt. %, particularly less than 2 wt. %. Lightening preparations containing less than 0.1 wt. % of water can be most particularly preferred according to the invention. The agent (M2) is preferably formulated as a powder or anhydrous paste.

Bleach intensifiers of the alkyl carbonate and carbamate and silyl carbonate and silyl carbamate type can be used in the anhydrous compositions as bleach intensifiers and are represented by compounds of the formula (BV)

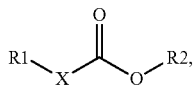

(BV)

wherein R1 is a saturated or unsaturated, straight-chain, branched or cyclic, substituted or unsubstituted hydrocarbon residue or a substituted or unsubstituted aryl group or a substituted or unsubstituted heterocyclic compound, X is an O or NR3 group, wherein R3 is a hydrogen atom, a saturated or unsaturated, straight-chain, branched or cyclic, substituted or unsubstituted hydrocarbon residue or a substituted or unsubstituted silyl group or a substituted or unsubstituted aryl group or a substituted or unsubstituted heterocyclic compound, and R2 is a hydrogen atom, an alkali metal atom, particularly sodium, or an $SiR_3$ group wherein each R is independently a hydrogen atom, a saturated or unsaturated, straight-chain, branched or cyclic, substituted or unsubstituted hydrocarbon residue or a trialkylsilyl group, preferably a trimethylsilyl group, or a substituted or unsubstituted aryl group or a substituted or unsubstituted heterocyclic compound or a halogen, a substituted or unsubstituted hydroxyl or amino group.

In formula (By), R1 preferably is a substituted or unsubstituted, straight-chain or branched alkyl, alkenyl or alkynyl residue, with hydroxyl, amino, nitro, sulfonic acid groups or halogens being preferably suitable as substituents. Further preferred residues R1 are phenyl and benzyl residues and further substituted representatives. Compositions that are particularly preferably used according to the invention are those wherein R1 in formula (BV) is chosen from methyl, ethyl, n-propyl, i-propyl, n-butyl, i-butyl, t-butyl as well as hydroxymethyl and hydroxyethyl. Preferred residues R2 and R3 in formula (BV) are hydrogen, substituted or unsubstituted, straight-chain or branched alkyl residues as well as trialkylsilyl residues. Of these, hydrogen, methyl, ethyl, t-butyl and trimethylsilyl residues are preferred.

At least one compound chosen from acetic acid, lactic acid, tartaric acid, citric acid, salicylic acid and ortho-phthalic acid can preferably be included in compositions according to the invention as further additional bleach intensifiers.

In a further preferred embodiment the agent (M2) can contain at least one cationic pyridinium derivative as bleaching strength intensifier. Preferred compounds are 4-acyl pyridinium derivatives and 2-acyl pyridinium derivatives. 2-Acetyl-1-methylpyridinium-p-toluenesulfonate and 4-acetyl-1-methylpyridinium-p-toluenesulfonate are preferred in particular. Further preferred cationic pyridinium derivatives are cationic 3,4-dihydroisoquinolinium derivatives. N-Methyl-3,4-dihydroisoquinolinium-p-toluenesulfonate is preferred in particular.

Bleaching strength intensifiers used in addition to or instead of peroxo compounds are included in cosmetic agents according to the invention preferably in amounts from 0.05 to 10 wt. %, particularly from 0.2 to 5 wt. %, based on total weight of the ready-to-use agent.

To further increase the lightening capacity at least one optionally hydrated $SiO_2$ compound can also be added to the composition as a bleach intensifier. Although even small amounts of optionally hydrated $SiO_2$ compounds increase the lightening capacity, preferably the optionally hydrated $SiO_2$ compounds are used in amounts from 0.05 wt. % to 15 wt. %, more preferably from 0.15 wt. % to 10 wt. %, and most preferably from 0.2 wt. % to 5 wt. %, based on the anhydrous composition according to the invention. Specified amounts indicate the content of $SiO_2$ compounds (excluding their water component) in the agents.

Preferred optionally hydrated $SiO_2$ compounds are silicic acids, oligomers and polymers thereof and salts thereof. Preferred salts are the alkali salts, particularly potassium and sodium salts. Sodium salts are most particularly preferred. The optionally hydrated $SiO_2$ compounds can be present in various forms.

According to the invention, $SiO_2$ compounds are preferably used in the form of silica gels or more preferably as water glass. In some cases these $SiO_2$ compounds can be present in aqueous solution. Most particularly preferred according to the invention are water glasses formed from a silicate of the formula $(SiO_2)_n(Na_2O)_m(K_2O)_p$, where n is a positive rational number and m and p are independently a positive rational number or 0, with the provisos that at least one of m or p is different from 0 and that the ratio of n to the sum of m and p is from 1:4 to 4:1. In particular, metasilicates, which are characterized according to the formula above by a ratio of n to the sum of m and p of $\leq 1$ and which can be regarded as chain-like polymeric structures of the anion $[SiO_3]^{2-}$, can be preferably used. Sodium metasilicate of the formula $[NaSiO_3]_x$ is particularly preferred.

In addition to components described by the empirical formula, water glasses can also contain small amounts of other additives such as phosphates or magnesium salts.

In a further embodiment of the present invention the agent (M2) contains coloring components as the color-changing component. The agents can therefore additionally contain at least one coloring component preferably chosen from (1) at least one oxidation dye precursor and/or (2) at least one substantive dye.

Preferred agents for changing the color of keratinic fibers thus contain at least one oxidation dye precursor.

Lightening agents according to the invention contain as oxidation dye precursor at least one oxidation dye precursor of the developer type (developer component), preferably in combination with at least one oxidation dye precursor of the coupler type (coupler component).

Preferred oxidation dye precursors of the developer type are p-phenylenediamine derivatives. Particularly preferred p-phenylenediamines are chosen from one or more compounds of p-phenylenediamine, p-toluoylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane and the physiologically tolerable salts thereof. Most particularly preferred p-phenylenediamine derivatives according to the invention are selected from at least one compound of the group p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine and the physiologically tolerable salts of these compounds.

It can further be preferred according to the invention to use as the developer component compounds having at least two aromatic nuclei which are substituted with amino and/or hydroxyl groups. Preferred binuclear developer components are selected in particular from at least one of the following compounds: N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl)tetramethylenediamine, N,N'-bis-(4-(methylamino)phenyl)tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl)piperazine, N-(4'-aminophenyl)-p-phenylenediamine and 1,10-bis-(2',5'-diaminophenyl)-1,4,7,10-tetraoxadecane and the physiologically tolerable salts thereof. Most particularly preferred binuclear developer components are selected from N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane or one of the physiologically tolerable salts of these compounds.

It can also be preferred to use a p-aminophenol derivative or one of its physiologically tolerable salts as the developer component. Preferred p-aminophenols are in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol and physiologically tolerable salts thereof. Most particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

The developer component can further be chosen from o-aminophenol and derivatives thereof, such as 2-amino-4-methylphenol, 2-amino-5-methylphenol or 2-amino-4-chlorophenol.

The developer component can furthermore be chosen from heterocyclic developer components such as from pyrimidine derivatives, pyrazole derivatives, pyrazolopyrimidine and pyrazolopyrazole derivatives and physiologically tolerable salts thereof.

Particularly preferred pyrimidine derivatives include the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Particularly preferred pyrazole derivatives include 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and physiologically tolerable salts thereof, particularly 4,5-diamino-1-(2-hydroxyethyl)pyrazole.

Preferred pyrazolopyrimidines include pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine and the physiologically tolerable salts thereof and their tautomeric forms, if a tautomeric equilibrium exists. A preferred pyrazolopyrazole derivative is 2,3-diamino-6,7-dihydro-1H,5H-pyrazolo[1,2-a]pyrazol-1-one.

Particularly preferred developer components include at least one of p-phenylenediamine, p-toluoylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one and the physiologically tolerable salts of these compounds.

Most particularly preferred developer components here are p-toluoylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically tolerable salts thereof.

Developer components are preferably used in an amount of from 0.0001 to 0.5 wt. %, preferably 0.001 to 0.2 wt. %, based on total weight of the ready-to-use agent.

In the context of oxidative dyeing, coupler components develop no significant color on their own but always need the presence of developer components. It is therefore preferable that, with the use of at least one coupler component, at least one developer component is additionally used. Coupler components within the meaning of the invention permit at least one substitution of a chemical residue of the coupler with the oxidized form of the developer component. A covalent bond forms between the coupler and developer component in this process. Couplers are preferably cyclic compounds bearing at least two groups on the cycle, selected from (i) optionally substituted amino groups and/or (ii) hydroxyl groups. If the cyclic compound is a six-membered ring (preferably aromatic), the groups are preferably in ortho- or meta-position to one another.

Coupler components according to the invention are preferably chosen from: m-aminophenol, o-aminophenol, m-diaminobenzene, o-diaminobenzene and/or derivatives thereof; naphthalene derivatives having at least one hydroxyl group; di- or trihydroxybenzene; pyridine derivatives; pyrimidine derivatives; certain indole derivatives and indoline derivatives; pyrazolone derivatives (for example 1-phenyl-3-methylpyrazol-5-one); morpholine derivatives (for example 6-hydroxybenzomorpholine or 6-aminobenzomorpholine); quinoxaline derivatives (for example 6-methyl-1,2,3,4-tetrahydroquinoxaline), as well as mixtures of two or more compounds from one or more of these components.

Particularly preferred m-aminophenol coupler components are chosen from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3-dihydroxy-5-(methylamino)benzene, 3-ethylamino-4-methylphenol, 2,4-dichloro-3-aminophenol and the physiologically tolerable salts of all aforementioned compounds.

Particularly preferred m-diaminobenzene coupler components are chosen from m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and the physiologically tolerable salts of all aforementioned compounds.

Particularly preferred o-diaminobenzene coupler components are chosen from 3,4-diaminobenzoic acid and 2,3-diamino-1-methylbenzene and the physiologically tolerable salts of all aforementioned compounds.

Preferred naphthalene derivatives containing at least one hydroxyl group are chosen from 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene.

Preferred di- or trihydroxybenzenes and derivatives thereof are chosen from resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Particularly preferred pyridine derivatives are chosen from 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine, and the physiologically tolerable salts of the aforementioned compounds.

Preferred pyrimidine derivatives are chosen from 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and the physiologically tolerable salts of the aforementioned compounds.

Particularly preferred indole derivatives are chosen from 4-hydroxyindole, 6-hydroxyindole and 7-hydroxyindole and the physiologically tolerable salts of the aforementioned compounds.

Particularly preferred indoline derivatives are chosen from 4-hydroxyindoline, 6-hydroxyindoline and 7-hydroxyindoline and the physiologically tolerable salts of the aforementioned compounds.

Particularly preferred coupler components according to the invention are chosen from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5- dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically tolerable salts of the aforementioned compounds.

Resorcinol, 2-methylresorcinol, 5-amino-2-methylphenol, 3-aminophenol, 2-(2,4-diaminophenoxy)ethanol, 1,3-bis(2, 4-diaminophenoxy)propane, 1-methoxy-2-amino-4-(2'-hydroxyethylamino)benzene, 2-amino-3-hydroxypyridine and 1-naphthol and one of the physiologically acceptable salts thereof are most particularly preferred.

Coupler components are preferably used in an amount of from 0.0001 to 0.5 wt. %, preferably 0.001 to 0.2 wt. %, based on total weight of the ready-to-use agent.

Developer components and coupler components are generally used in approximately molar amounts to one another. Although molar use has proved convenient, a certain excess of individual oxidation dye precursors is not disadvantageous so that developer components and coupler components can be in a molar ratio of 1 to 0.5 to 1 to 3, particularly 1 to 1 to 1 to 2.

Agents according to the invention can furthermore contain at least one substantive dye. These are dyes which attach directly to hair and require no oxidative process to develop the color. Substantive dyes can be divided into anionic, cationic and non-ionic substantive dyes. They are conventionally nitrophenylene diamines, nitroaminophenols, azo dyes, anthraquinones or indophenols. Substantive dyes are each preferably used in an amount from 0.0001 to 0.2 wt. %, preferably 0.001 to 0.1 wt. %, relative to the complete application preparation. The total amount of substantive dyes is preferably at most 0.1 wt. %.

Preferred anionic substantive dyes include compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes such as Basic Blue 7, Basic Blue 26, Basic Violet 2 and Basic Violet 14, aromatic systems which are substituted with a quaternary nitrogen group such as Basic Yellow 57, Basic Red 76, Basic Blue 99, Basic Brown 16 and Basic Brown 17, as well as substantive dyes containing a heterocyclic compound having at least one quaternary nitrogen atom, particularly Basic Yellow 87, Basic Orange 31 and Basic Red 51. Cationic substantive dyes sold under the trademark Arianor® are likewise most particularly preferred cationic substantive dyes according to the invention.

Non-ionic nitro and quinone dyes and neutral azo dyes in particular are suitable as non-ionic substantive dyes. Preferred non-ionic substantive dyes include compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Preferred dye combinations according to the invention include those having at least a combination of tetrabromophenol blue and Acid Red 92; tetrabromophenol blue and Acid Red 98; tetrabromophenol blue and Acid Red 94; tetrabromophenol blue and Acid Red 87 or tetrabromophenol blue and Acid Red 51.

Ready-to-use agents according to the invention are preferably aqueous, free-flowing preparations. The agents can furthermore contain all active ingredients, additives and auxiliary substances known for such preparations. Ready-to-use agents as a mixture of agent (M1) and (M2) can contain surface-active substances chosen from the aforementioned anionic, non-ionic, zwitterionic and amphoteric surfactants.

Likewise preferred according to the invention are cationic surfactants of the quaternary ammonium compound, esterquat and amidoamine type. Preferred quaternary ammonium compounds are ammonium halides, in particular chlorides and bromides, such as alkyltrimethylammonium chlorides, dialkyldimethylammonium chlorides and trialkylmethylammonium chlorides, as well as imidazolium compounds known under the INCI names Quaternium-27 and Quaternium-83. Other useful cationic surfactants according to the invention are the quaternized protein hydrolysates. Alkylamidoamines are conventionally produced by amidation of natural or synthetic fatty acids and fatty acid cuts with dialkyl amino amines and, in addition to a good conditioning effect, have good biodegradability, such as stearamidopropyl dimethylamine. Likewise preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. Such products are sold, for example, under the trademarks Stepantex, Dehyquart and Armocare. The products Armocare VGH-70, an N,N-bis(2-palmitoyloxyethyl)dimethylammonium chloride, as well as Dehyquart F-75, Dehyquart C-4046, Dehyquart L80 and Dehyquart AU-35 are examples of such esterquats.

Cationic surfactants are contained in agents used according to the invention preferably in amounts from 0.05 to 10 wt. %, relative to the complete agent. Amounts from 0.1 to 5 wt. % are particularly preferred.

In a preferred embodiment non-ionic, zwitterionic and/or amphoteric surfactants and mixtures thereof can be preferred.

According to the invention, the oxidizing agent preparation can also be applied to the hair together with a catalyst which activates oxidation of the dye precursors, for example, through atmospheric oxygen. Such catalysts include certain enzymes, iodides, quinones or metal ions. Suitable enzymes are, for example, peroxidases, which can significantly strengthen the action of small amounts of hydrogen peroxide. A use of certain metal ions or complexes can likewise be preferred. Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$, $Ce^{4+}$, $V^{3+}$, $Co^{2+}$, $Ru^{3+}$ and $Al^{3+}$. $Zn^{2+}$, $Cu^{2+}$ and $Mn^{2+}$ are particularly suitable.

It has also proved advantageous for the oxidizing agent preparations to contain at least one stabilizer or complexing agent. Particularly preferred stabilizers are phenacetin, alkali benzoates (sodium benzoate) and salicylic acid.

Also preferred is the use of complexing agents. Complexing agents are substances which are capable of complexing metal ions. Preferred complexing agents are chelating agents, that is, substances which form cyclic compounds with metal ions, wherein an individual ligand occupies more than one coordination site on a central atom (i.e., it is at least "bidentate").

Common preferred chelating agents include polyoxycarboxylic acids, polyamines, ethylenediaminetetraacetic acid (EDTA), nitrilotriacetic acid (NTA) and hydroxyethane diphosphonic acids or the alkali salts thereof. Complexing polymers, that is, polymers bearing functional groups either in the main chain itself or laterally thereto which can act as ligands and react with suitable metal atoms, generally forming chelate complexes, can also be used according to the invention. The polymer-bonded ligands of the metal complexes formed can derive from just one macromolecule or can belong to various polymer chains. Preferred complexing agents are nitrogen-containing polycarboxylic acids, particularly EDTA, and phosphonates, preferably hydroxyalkane or aminoalkane phosphonates, and in particular 1-hydroxyethane-1,1-diphosphonate (HEDP) or the disodium or tetrasodium salt thereof and/or ethylenediamine tetramethylene phosphonate (EDTMP) or the hexasodium salt thereof and/or diethylenetriamine pentamethylene phosphonate (DTPMP) or the heptasodium or octasodium salt thereof.

Other active ingredients, auxiliary substances and additives for use according to the invention include:

non-ionic polymers such as vinyl pyrrolidinone/vinyl acrylate copolymers, polyvinyl pyrrolidinone and vinyl pyrrolidinone/vinyl acetate copolymers and polysiloxanes;

zwitterionic and amphoteric polymers such as acrylamidopropyl trimethylammonium chloride/acrylate copolymers and octylacrylamide/methyl methacrylate/tert-butyl aminoethyl methacrylate/2-hydroxypropyl methacrylate copolymers;

anionic polymers such as polyacrylic acids, crosslinked polyacrylic acids, vinyl acetate/crotonic acid copolymers, vinyl pyrrolidinone/vinyl acrylate copolymers, vinyl acetate/butyl maleate/isobornyl acrylate copolymers, methyl vinyl ether/maleic anhydride copolymers and acrylic acid/ethyl acrylate/N-tert-butyl acrylamide terpolymers;

thickening agents such as agar-agar, guar gum, alginates, xanthan gum, gum arabic, karaya gum, carob seed meal, linseed gums, dextrans, cellulose derivatives, for example methyl cellulose, hydroxyalkyl cellulose and carboxymethyl cellulose, starch fractions and derivatives such as amylose, amylopectin and dextrins, clays such as bentonite, or fully synthetic hydrocolloids such as polyvinyl alcohol;

texturizing agents such as sugars, maleic acid and lactic acid and consistency modifiers such as sugar esters, polyol esters or polyol alkyl ethers;

protein hydrolysates, in particular elastin, collagen, keratin, milk protein, soya protein and wheat protein hydrolysates, condensation products thereof with fatty acids;

perfume oils;

cyclodextrins;

solvents and solubilizers such as ethanol, isopropanol, ethylene glycol, propylene glycol, glycerol, dimethyl isosorbide and diethylene glycol;

defoaming agents such as silicones;

dyes and pigments to color the agent;

anti-dandruff active ingredients such as piroctone olamine, zinc omadine and climbazole;

light stabilizers, particularly derivatized benzophenones, cinnamic acid derivatives and triazines;

active ingredients such as allantoin, pyrrolidone carboxylic acids, cholesterol and salts thereof;

other fats and waxes such as beeswax, montan wax and paraffins;

swelling and penetrating substances such as glycerol, propylene glycol monoethyl ether, carbonates, hydrogen carbonates, guanidines, ureas, as well as primary, secondary and tertiary phosphates;

opacifiers such as latex, styrene/PVP and styrene/acrylamide copolymers;

pearlescent agents such as ethylene glycol mono- and distearate as well as PEG-3 distearate;

stabilizing agents for hydrogen peroxide and other oxidizing agents;

blowing agents such as propane-butane mixtures, $N_2O$, dimethyl ether, $CO_2$ and air; and antioxidants.

The person skilled in the art will select these further substances in accordance with the desired properties of the agents. Regarding further optional components and the amounts of these components used, reference is made to relevant manuals known to one skilled in the art, for example, Kh. Schrader, Grundlagen and Rezepturen der Kosmetika, $2^{nd}$ Edition, Hüthig Buch Verlag, Heidelberg (1989).

Ready-to-use agents comprising the two-phase agent (M1) and color-changing agent (M2) preferably have a pH in a range of from 6 to 12. Preferred agents according to the invention have an alkaline pH. A further preferred embodiment consists in that the ready-to-use agent has a pH of from 7.0 to 12.0, preferably 8.0 to 11.0. The pH values within the meaning of the present invention are pH values measured at a temperature of 22° C.

The pH is conventionally adjusted with pH adjusters. Acidifying and alkalizing agents commonly used in cosmetics are familiar to one skilled in the art for adjusting pH. Alkalizing agents that can be used for adjusting pH are typically chosen from inorganic salts, particularly alkali and alkaline-earth metals, organic alkalizing agents, particularly amines, basic amino acids and alkanol amines, and ammonia. Preferred acidifying agents include food acids such as citric acid, acetic acid, malic acid or tartaric acid, as well as dilute mineral acids.

Organic alkalizing agents that can be used according to the invention are preferably chosen from alkanol amines from primary, secondary or tertiary amines having a $C_2$-$C_6$ alkyl parent substance bearing at least one hydroxyl group. Most particularly preferred alkanol amines according to the invention are chosen from 2-aminoethan-1-ol (monoethanolamine), 2-amino-2-methylpropan-1-ol and 2-amino-2-methylpropane-1,3-diol. A preferred alkanol amine is monoethanolamine. Suitable basic amino acids are lysine, arginine and ornithine. The inorganic alkalizing agent according to the invention is preferably chosen from sodium hydroxide, potassium hydroxide, calcium hydroxide, barium hydroxide, sodium phosphate, potassium phosphate, sodium silicate, potassium silicate, sodium carbonate and potassium carbonate.

Compositions according to the invention preferably contain alkalizing agents in amounts from 0.2 to 25 wt. %, particularly 0.5 to 10 wt. %.

Application temperatures can be in a range of from 15 to 40° C. After a contact time of 2 to 60, preferably 5 to 45 minutes, the bleaching agent is removed from the hair by rinsing. There is no need to wash with a shampoo afterwards if a carrier with high surfactant content is used.

Depending on the composition of agents (M1) and (M2), it can be preferable according to the invention to prepare the agents only immediately prior to application by mixing agent (M1) and agent (M2). This is particularly advantageous if there are incompatibilities between individual ingredients. For that reason a preferred packaging format of the ready-to-use agent is a separate packaging unit wherein agents (M1) and (M2) are packaged separately from each other.

The present invention also provides for a kit of parts having at least two containers separately packaged from each other—a first container (C1) containing a cosmetic agent (M1) according to the first subject-matter of the invention and a second container (C2) containing a color-changing preparation (M2) containing in a cosmetic carrier at least one color-changing component.

A container within the context of the present invention is understood to be a casing in the form of an optionally reclosable bottle, a tube, a can, a packet, a sachet or similar casings. There are no restrictions according to the invention on the casing material. The casings are preferably glass or plastic casings. An embodiment in which the casing of the container containing agent (M1) is transparent to the user, enabling the two-phase agent (M1) to be viewed, is particularly preferred. A preferred embodiment of the kit of parts therefore has the characterizing feature that the first container (C1) containing the agent (M1) has a transparent packaging, preferably a transparent plastic packaging.

A further embodiment of this subject-matter of the invention is provided if the agent (M2) from container (C2) is the coloring preparation and contains as the color-changing component at least one oxidation dye precursor and/or at least one substantive dye and/or at least one lightening agent.

It can further be particularly advantageous according to the invention if the cited kit of parts contains at least one further hair treatment agent in a separate container, in particular a conditioning agent. The packaging unit can moreover encompass application aids, such as combs, brushes or applicators, personal protective clothing, in particular disposable gloves, and optionally instructions for use.

Regarding the preferred embodiments of agents (M1) and (M2), the above embodiments of the aforementioned subject-matters of the invention apply with necessary alterations.

When using the kit of parts, it makes no difference whether the two phases of agent (M1) are first mixed thoroughly by vigorously shaking for a short time and agent (M2) is added before the phases separate again in order to provide the ready-to-use color-changing preparation, or whether agent (M2) is first added to agent (M1) and then the ready-to-use mixture is prepared by mixing thoroughly.

For improved mixing it is advantageous if container (C1) containing the two-phase agent (M1) has a reclosable opening such as a snap or screw closure. This makes it easier to add the color-changing agent from container (C2), which is preferably in the form of a packet or sachet for anhydrous, particularly powdered color-changing agents, or in the form of a tube for free-flowing color-changing agents.

Preferably, the individual preparations are mixed and the ready-to-use agent applied contemporaneously to the keratinic fibers.

A further subject-matter of the invention is therefore a method for changing the color of keratinic fibers, particularly human hair, wherein, from a kit of parts according to the aforementioned subject-matter of the invention, the contents of container (C2) are added to container (C1), container (C1) is closed again and then shaken, and the resulting ready-to-use color-changing agent in container (C1) is then applied to the fibers, left on the fibers for a contact time of 5 to 60 min, and finally rinsed out.

For a coloring agent, the preferred contact time is 5 to 40 min, preferably 10 to 30 min. For lightening or bleaching color-changing agents, the preferred contact time is 30 to 60 min, preferably 40 to 60 min.

A further subject-matter of the invention is a method for changing the color of keratinic fibers, particularly human hair, wherein, from a kit of parts according to the aforementioned subject-matter of the invention, container (C1) is shaken, the resulting mixture of phases (I) and (II) is then immediately mixed thoroughly with a coloring preparation from container (C2), the resulting ready-to-use color-changing agent is then applied to the fibers, left on the fibers for a contact time of 5 to 60 min, and finally rinsed out.

In the context of this subject-matter of the invention, the aforementioned statements apply in an analogous manner with the necessary alterations.

The examples below are intended to further illustrate the subject-matter of the present invention without in any way limiting it.

EXAMPLES

1. Formulations

| Raw materials | wt. % |
| --- | --- |
| Gluadin WQ | 1.00 |
| Na benzoate | 0.10 |
| Glycine | 0.20 |
| Puricare LS 9658 | 0.10 |
| D-Panthenol 75% | 0.50 |
| Luviquat FC 550 | 1.00 |
| Genamin CTAC | 0.50 |
| Lactic acid | 0.66 |
| Dow Corning 5225 C Formulation Aid | 3.50 |
| Dow Corning 556 | 1.00 |
| Dow Corning DB 1411 | 3.50 |
| Parsol SLX | 1.00 |
| Dipicolinic acid | 0.10 |
| Disodium pyrophosphate | 0.03 |
| Turpinal SL | 1.50 |
| Dow Corning DB 110 A | 0.07 |
| Aculyn 33A | 12.00 |
| Hydrogen peroxide 50% | 22.40 |
| Perfume | qs |
| Water | to 100 |

Gluadin WQ (approx. 31% active substance content; INCI name: Laurimonium Hydroxypropyl Hydrolyzed Wheat Protein; Cognis); Puricare LS 9658 (approx. 0.1-1% active substance content; INCI name: Aqua, Glycerine, Moringa Pterygosperma Seed Extract; Laboratoires Serobiologiques); Luviquat FC 550 (approx. 40% active substance content; INCI name: Polyquaternium-16; BASF); Genamin CTAC (approx. 30% active substance content; INCI name: Cetrimonium Chloride; Clariant); Dow Corning 5225 C (INCI name: Cyclomethicone, PEG/PPG-18/18 Dimethicone; Dow Corning); Dow Corning 556 (INCI name: Phenyl Trimethicone; Dow Corning); Dow Corning DB 1411 (INCI name: Cyclomethicone, Dimethicone; Dow Corning); Parsol SLX (INCI name: Polysilicone-15; DSM); Turpinal SL (approx. 60% active substance content; INCI name: Etidronic Acid, Aqua; Solutia); Aculyn 33 (approx. 28% solids in water; INCI name: Acrylates Copolymer; Rohm & Haas); Dow Corning DB 110 A (INCI name: Dimethicone; Dow Corning).

We claim:

1. A cosmetic agent for the treatment of keratinic fibers comprising:
   at least two phases separated from each other,
   wherein the first phase (I) is an aqueous phase containing at least one chemical oxidizing agent, and
   wherein the second phase (II) is a hydrophobic phase containing at least one silicone oil.

2. Agent according to claim 1, wherein the chemical oxidizing agent of phase (I) is chosen from hydrogen peroxide and/or one of its solid addition products with inorganic and/or organic compounds.

3. Agent according to claim 1, wherein the silicone oil of the hydrophobic phase (II) is chosen from dimethicones and cyclomethicones.

4. Agent according to claim 1 further comprising nonionic, anionic, zwitterionic and/or amphoteric surfactants and/or emulsifiers in an amount of up to 5 wt. %, based on total weight of the agent.

5. Agent according to claim 4 wherein the surfactants and/or emulsifiers are present in an amount of up to 1 wt. %, based on total weight of the agent.

6. Agent according to claim 1 further comprising at least one care component that is largely soluble in the silicone oil and chosen from oil-soluble care substances, oil-soluble vitamins and triglycerides.

7. Kit of parts comprising:
   a first container (C1) comprising a cosmetic preparation according to claim 1, and
   a second container (C2) comprising a color-changing preparation having in a cosmetic carrier at least one color-changing component,
   wherein the two containers are packaged separately from each other.

8. Kit of parts according to claim 7, wherein the first container (C1) has a transparent packaging.

9. Kit of parts according to claim 7, wherein the color-changing component is at least one oxidation dye precursor and/or at least one substantive dye and/or at least one lightening agent.

10. Method for changing the color of keratinic fibers, comprising:
    adding from a kit of parts according to claim 6 the contents of container (C2) to container (C1),
    closing container (C1) and shaking it,
    applying the resulting ready-to-use color-changing agent in container (C1) to the fibers,
    leaving the color-changing agent on the fibers for a contact time of 5 to 60 min, and
    rinsing out the color-changing agent.

11. Method for changing the color of keratinic fibers, comprising:
    shaking from a kit of parts according to claim 7 container (C1),
    mixing the resulting mixture of phases (I) and (II) with a coloring preparation from container (C2),
    applying the resulting ready-to-use color-changing agent to the fibers,
    leaving the color-changing agent on the fibers for a contact time of 5 to 60 min, and
    rinsing out the color-changing agent.

* * * * *